US007947269B2

(12) United States Patent
Bolckmans et al.

(10) Patent No.: US 7,947,269 B2
(45) Date of Patent: *May 24, 2011

(54) MITE COMPOSITION, USE THEREOF, METHOD FOR REARING A PHYTOSEIID PREDATORY MITE, REARING SYSTEM FOR REARING SAID PHYTOSEIID PREDATORY MITE AND METHODS FOR BIOLOGICAL PEST CONTROL ON A CROP

(75) Inventors: Karel Jozef Florent Bolckmans, Hoogstraten (BE); Yvonne Maria van Houten, Naaldwijk (NL)

(73) Assignee: Koppert B.V., Berkel En Rodenrijs (NL)

( * ) Notice: Subject to any disclaimer, the term of this patent is extended or adjusted under 35 U.S.C. 154(b) by 279 days.

This patent is subject to a terminal disclaimer.

(21) Appl. No.: 11/793,579

(22) PCT Filed: Dec. 31, 2004

(86) PCT No.: PCT/NL2004/000929
§ 371 (c)(1),
(2), (4) Date: Sep. 12, 2007

(87) PCT Pub. No.: WO2006/071107
PCT Pub. Date: Jul. 6, 2006

(65) Prior Publication Data
US 2008/0118476 A1 May 22, 2008

(51) Int. Cl.
*A01K 67/033* (2006.01)
*A01N 63/02* (2006.01)
*A01P 7/00* (2006.01)
(52) U.S. Cl. ............. 424/93.7; 514/789; 800/8; 800/13; 119/6.5
(58) Field of Classification Search .................. None
See application file for complete search history.

(56) References Cited

U.S. PATENT DOCUMENTS

| 4,646,683 | A |   | 3/1987  | Maedgen, Jr. |     |
|-----------|---|---|---------|--------------|-----|
| 5,192,546 | A | * | 3/1993  | Abercrombie  | 424/405 |
| 6,129,935 | A |   | 10/2000 | White et al. |     |
| 2005/0042244 | A1 | * | 2/2005 | Hino et al.  | 424/405 |
| 2005/0178337 | A1 | * | 8/2005 | Wright       | 119/6.5 |

FOREIGN PATENT DOCUMENTS

| GB | 2168680      | 6/1986  |
| GB | 2393890      | 4/2004  |
| JP | 3108433      | 5/1991  |
| JP | 08040814     | 2/1996  |
| WO | WO99/59402 A1 | 11/1999 |

OTHER PUBLICATIONS

Simberloff et al. (Ecology. 1969; 50 (2): 278-296).*
Simberloff et al. (Ecology. 1970; 51 (5): 934-937).*
Piechnik et al. (Oikos. 2008; 117: 665-674).*
Abou-Awad et al., "Effects of artificial and natural diets on the development and reproduction of two phytoseiid mites *Amblyseius gossipi* and *Amblyseius swirskii* (Acari: Phytoseiidae)," Insect Sci. Applic., 1992, 13(3):441-445.
Castagnoli et al., "Short-term changes in consumption and oviposition rate of *Neoseiulus californicus* strains (Acari: Phytoseiidae) after a diet shift," Experimental and Applied Acarology, 2001, 25(12):969-983.
Rasmy et al., "Cannabalism and insterspecific predation of the phytoseiid mite, *Amblyseius swirskii*," J Pest Sci., 2004, 77(1):23-25.
Shih, "Automatic mass-rearing of the *Amblyseius womersleyi* (Acari:Phytoseiidae)," Experimental and Applied Acarology, 2001, 25(5):425-440.
Abou-Awad B.A. et al. "Impact of two eriophyoid fig mites, *aceria ficus* and *rhyncaphytoptus ficifoliae*, as prey on postembryonic development and oviposition rate of the predacious mite amblyseius swirskii" Acarologia, vol. XL fasc. 4 pp. 367-371 (1999).
Abou-Awad B.A. et al. "Environmental management and biological aspects of the two eriophyoid fig mites *aceria ficus* (cotte) and *rhyncaphytoptus ficifoliae* Keifer in Egypt" Anz. Schädlingskunde / J. Pest Science vol. 73, pp. 5-12, Blackwell Wissenschafts-Verlag Berlin ISSN 1436-5693 US Copyright Clearance Center code statement 1436-5693/00/7301-0005 (2000).
A. Koike et al., "Phyto-Trap" NII electronic Library Service Jpn. J. Appl. Entomol. Zool. vol. 44 pp. 35-40 (1999).
A. Enkegaard "Newsletter on biological control in greenhouses—several articles (New phytoseiid predators)" Sting vol. 26, Danish Institute of Agricultural Sciences (2004).
Beglyarov, et al. "The flour mite [*Acarus siro*] for mass breeding of phytoseiids." Zashchita-Rastenii No. 10, p. 25 (1990).
Bennison et al., "Integrated control of Frankliniella occidentalis (Pergande) in UK cucumber crops-evaluation of a controlled release system of introducing Amblyseius cucumeris." Med. Fac. Landbouww. Rijksuniv. Gent, vol. 56, No. 2A, 1991, pp. 251-255 (1991).
Bennison et al., "Recent developments with integrated control of thrips on cucumber in the United Kingdom." International Organisation for Biological and Integrated Control of noxious animals and plants, Glasshouse pests SROP/WPRS BULL. XIII/5 1990, pp. 19-26 (1990).
Castagnoli et al., "Effect of long term feeding history on functional and numerical responses of *Neoseiulus californicus* (Acari, Phytoseiidae)" Experimental and Applied Acarology. vol. 23, pp. 217-234 (1999).
Chant et al., "A review of the subfamily *Ablyseiinae Muma* (Acari;Phytoseiidae) Part I. Neoseiulini new tribe" International Journal of Acarology vol. 29: pp. 3-46 (2003).
Chant et al., "A review of the subfamily *Amblyseiinae Muma* (Acari:Phytoseiidae) Part III. The tribe Amblyseiini Wainstein, subtribe Amblyseiina N. Subtribe" International Journal of Acarology vol. 30: pp. 171-228 (2004).

(Continued)

*Primary Examiner* — Shanon A Foley
(74) *Attorney, Agent, or Firm* — Bozicevic, Field & Francis LLP; Bret E. Field

(57) ABSTRACT

The present invention relates to a novel mite composition comprising a population of a phytoseiid predatory mite species and a factitious host population, which may be employed for rearing said phytoseiid predatory mite species or for releasing the pyrltoseiid predatory mite species in a crop. According to further aspects the invention relates to a method for rearing a phytoseiid predatory mite species, to the use of the mite composition and to a method for biological pest control in a crop, which employ the mite composition.

30 Claims, 2 Drawing Sheets

OTHER PUBLICATIONS

Chmielewski W., "Morfologia, biologia I ekologia *Carpoglyphus lactis* (L. 1758) (Glycyphagidae, Acarina) Summary morphology, biology and ecology of *carpoglyphus lactis* (L. 1758) (Glycyphagidae, acarina) P 164-166; Prace Nauk. Inst. Ochrony Roslin 13 vol. 13, No. 2, 1971, pp. 63-166 (abstract) (1971).

Chmielewski W., "Wyniki badan morfologicznych, biologicznych I ekologicznych nad rortoczkiem suszowym—*Carpoglyphus lactis*" Prace Nauk. Inst. Ochrony Roslin vol. 13, No. 1, 1971, pp. 87-106 (1971).

Chmielewski W., "Bionomics of *Carpoglyphus lactis* (Acari: Carpoglyphidae) on honey" In Bruin et al. (eds.) Ecology and evolution of Acari: 423-424 (1999).

Conjin et al., "Biological control of the bulb mite, *Rhizoglyphus robini*, by the predatory mite *Hypoaspis aculeifer*, on lilies: Implementation in practice" *Acta Horticluturae* vol. 430, pp. 619-624 (1997).

Croft et al., "Do literature records of predation reflect food specialization and predation types among phytoseiid mites (Acari: Phytoseiidae)?" Experimental and Applied Acarology vol. 22, pp. 467-480 (1998).

El Halawany et al., "Mites inhabiting date palms" Plant Protection Research Institute, Dokki, pp. 366-371 (2000).

El-Laithy et al, "Life table parameters of the two phytoseiid predators, *Amblyseius scutalis* (Athias-Henriot) and A. swirskii A.-H. (Acari, Phytoseiidae) in Egypt" J. Appl. Ent. 113 pp. 8-12 Verlag Paul Parey, Hamburg and Berlin ISSN 0931-2048 (1992).

El-Sherif et al., "Laboratory studies on Developmental and Oviposition Rates of Amblyseius Swirskii A.-H. (Acari: Phytoseiidae) Fed on *Tyrophagous putrescentiae* (Schrank) (Acari: Acaridea)" Arab Journal of Biotechnology vol. 2 No. 2 pp. 121-126 (1999).

Gerling et al., "Biological control of *Bemisia tabaci* using predators and parasitoids" Crop Protection vol. 20 pp. 779-799 (2001).

Gerson et al., "Mites (Acari) for Pest Control" Blackwell Science, Department of Entomology, Faculty of Agricultural Food and Environmental Sciences, Hebrew university, Rehovot, Israel / Systematic Entomology Laboratory, US Department of Agriculture, Agricultural Research Service, Beltsville, MD, USA Ingediend in KR dos 12: pp. 151-158 (2003).

Gilkeson L.A., "Mass rearing of phytoseiid mites for testing and commercial application" Anderson, T.E. & Leppla, N.C. (eds.), Advances in insect rearing for research and pest management. Boulder, Colorado, Westview Press. pp. 489-506; (1992).

Gilkeson L.A., "Advances in insect rearing for research and pest management" Anderson, T.E. & Leppla, N.C. (Eds). pp. 489-506 (1982).

Griffiths D.A., "A revision of the genus *Acarus* (Acaridae, Acarina)" Bull Brit. Mus. (nat. Hist.) (Zool), vol. 11, pp. 413-464 (1964).

Griffiths, D.A., "Some field habitats of mites of stored food products" Ann. Appl. Biol. vol. 48, pp. 134-144 (1960).

Hansen et al., "Possibilities and limitations of the use of Amblyseius Mckenziei Sch. & Pr. For biological control of thrips (Thrips tabaci Lind.) on glasshouse crops of cucumber" Department of Zoology, Danish Research Centre for plant protection, Lynby, Denmark pp. 145-150 (n.d.).

Houten et al., "Preselection of predatory mites to improve year-round biological control of western flower thrips in greenhouse crops" Entomologia Experimentalis et Applicata vol. 74, pp. 225-234 (1995).

Hughes A.M., "The mites of stored food and houses" 2nd ed. Ministry of Agriculture, Fisheries and Food, Technical Bulletin No. 9. His Majesty's Stationary Office, London, 287 pages; pp. 26, 27, 41 & 43 (1976).

Jacobson, R.J.,"Integrated pest management in cucumbers—prevention of establishment of Frankliniella occidentalis (pergande)" Med. Fac. Landbouww Univ. Gent 60/3a (1995).

Jarratt, J.H., "Stored-product pests" "Pest-Management Principles, pp. 61-67. Publication 2247 Mississippi State University Extension Service.http://msucares.com/pubs/publications/p2247ch7.pdf" (2001).

Karg W., "Die ökologische Differenzierung der Raubmilbenarten der Überfamilie Phytoseioidea Karg (Acarina, Parasitiformes) The ecological differentiation of the predatory mite species of the superfamily Phytoseioidea Karg (acarina, Parasitiformes)" Zool. Jb. Syst. 116, 31-46 VEB Gustav Fischer Verlag Jena (1989).

Kethley et al., "A terrestrial alicorhagiid mite (Acari: Acariformes)" Devonian of New York. Micropaleontology 35:367-373. (1989).

Knulle W., "Expression of a dispersal trait in a guild of mites colonizing transient habitats" Evolutionary Ecology 9: 341-353 (1995).

Lenteren et al., "Guidelines for quality control of commercially produced natural enemies" van Lenteren (ed.) Quality control and production of biological control agents—Theory and testing procedures. CABI Publishing, Wallingford: 265-303 (2003).

McMurtry et al., "Life-styles of phytoseiid mites and their roles in biological control" Annual Review of Entomology 42: 291-321 (1997).

McMurtry et al., "Nutritional ecology of insects, mites, spiders, and related invertebrates: Nutritional ecology of Phytoseiid Mites" John Wiley & sons, new York, ISBN: 047180617X pp. 609-644 (1987).

Meshkov, Yu.L. "Guidelines for rearing and using *Neoseiiulus cucumeris* (formerly *Amblyseius cucumeris*) predatory mite against pellucid strawberry mite" Collection of guidelines for plants protection, S.-Petersburg pp. 87-92 (1998).

Momen et al., "Biology and feeding behaviour of the predatory mite, amblyseius swirskii (Acari: Phytoseiidae)" National Research centre, plant protection department, Dokki Cairo, Egypt. Acarologia, t. XXXIV 34 fasc. 3 pp. 199-204 (1993).

Muma et al., "Phytoseiidae of Florida. Arthropods of Florida and neighbouring land areas" 6, Fla. Dept. Agr. Cons. Serv. Div. Plant Ind., Gainsville, 150 pages; p. 62, 100 (1970).

Nomikou et al., "Phytoseiid predators suppress populations of *Bemisia tabaci* on cucumber plants with alternative food" Experimental and Applied Acarology vol. 27: pp. 57-68 (2002).

Nomikou et al.,"Phytoseiid predators of whiteflies fed and reproduce on non-prey food sources" Exp. Appl. Acarol. 31:15-26. (2003).

Nomikou et al., "Phytoseiid predator of whitefly feeds on plant tissue" Experimental and Applied Acarology vol. 31, pp. 27-36 Kluwer Academic Publishers, printed in the Netherlands (2003).

Nomikou et al., "Phytoseiid predators as potential biological control agents for *Bemisia tabaci*" Exp. Appl. Acarol. vol. 25. pp. 271-291; (2001).

Norton et al., "Oribatid mite fossils from a terrestrial Devonian deposit near Gilboa, New York" Journal of Paleontology 62:259-269. (1988).

Oudemans "10.4.2 *Neoseiulus cucumeris*" Mites of Greenhouses Part III Beneficial Mites" ; Chapter 10 Phytoseiid Mites ; pp. 186-189 (n.d.).

Overmeer, W.P.J., "2.1.3.2. Alternative Prey and other food resources" Alternative prey and other food resources, p. 131-137. In Helle W, Sabelis MW, Spider mites, their biology, natural enemies and control vol. 1B. In Helle W, Sabel MW, Spider mites, Their biology, natural enemies and control vol. 1B. Amsterdam, Elsevier Science Publishers BV, Amsterdam (1995).

Palevsky et al., "Identification and evaluation of potential predators of the citrus rust mite, *phyllocoptruta oleivora*, in Israël" Systematic and Applied Acarology vol. 8, pp. 39-48 (2003).

Ramakers et al., "Manipulation of Phytoseiid thrips predators in the absence of thrips" IOBC/WPRS Bull. 13(5): 169-172 (1990).

Ramakers et al., "Start of commercial production and introduction of Amblyseius mckenziei Sch. & Pr. (Acarina: Phytoseiidae) for the control of Thrips tabaci lind. (Thysanoptera: Thripidae) in glasshouses" Mededelingen Faculteit Landbouwwetenschappen Rijksuniversiteit Gent vol. 47 No. 2, pp. 541-545 (1982).

Ramakers et al., "Mass production and introduction of Amblyseius mckenziei and A. cucumeris" IOBC WPRS Bulletin vol. 6, No. 3, 1983, pp. 203-206 (1983).

Ramakers et al., "Large scale introductions of Phytoseiid predators to control thrips on cucumber" Med. Fac. Landbouww. Rijksuniv. Gent vol. 54 No. 3a, pp. 923-929 (1989).

Rasmy et al., "A new diet for reproduction of two predaceous mites *amblyseius gossipi* and *agistemus exsertus* [acari: phytoseiidae, stigmaeidae]" Entomophaga vol. 32 No. 3 pp. 277-280 (1987).

Sampson C., "The commercial development of an *Amblyseius cucumeris* controlled release method for the control of *Frankliniella occidentalis* in protected crops" The 1998 Brighton Conference—Pests and diseases, vol. 5B-4, 1998, pp. 409-416 (1998).

Galun et al., "Meeting—The 10th conference of the entomological society of Israël—Agricultural Entomology (several articles)ARO—The volcani Center, Bet. Dagan, Israël; 27pp. (1997).

Solomon et al., "Rearing acaroid mites" Acarologia, fasc. H.S. 1964 (C.R.Ier Congres Int. D'Acarologie, Fort Collins, Col., U.S.A. (1963).

Swirski et al., "Laboratory studies on the feeding and development and reproduction of the predaceous mites *Amblyseius rubini*, Swirski and Amitai and *Amblyseius swirskii*, Athias on various food substances" Israel Journal of Agricultural Resea vol. 17, No. 2, pp. 101-119 (1967).

Teich Y., "Mites of the family Phytoseiidae as predators of the tabacco whitefly, *Bemisia tabaci*, Gennadius" Israel Journal of Agricultural Resea vol. 16, No. 3, pp. 141-142 (1966).

Treat, A.E., "Mites of moths and butterflies" Cornell University Press, Ithaca and London, pp. 272-293 (1975).

Van Rijn et al., "Pollen availability and its effect on the maintenance of polulations of *Amblyseius cucumeris*, a predator of thrips" Med. Fac. Landbouww. Rijksuniv. Gent. 55: 335-341 (1990).

Vanninen et al., "Performance of *Neoseiulus cucumeris* as a biocontrol agent of the Western Flower Thrips in cut roses" Bulletin of OILB/SROP 25:1, 289-292 (2002).

Wahab et al., "Mites associated with vegetable and ornamental plants in lower Egypt äcarina parasitiformes acariformes" Database Biosis Online! Biosciences information service, Philadelphia, PA, US—Database accession No. PREV197865057938, abstract, & Bulletin de la societe entomologigue D'Egypte, vol. 58, 1974, pp. 359-366, ISSN: 0373-3289 (1974).

Zdarkova E., "Section 4— Mites as pests of stored products. 14.1. Application of the bio-preparation 'cheyletin' in empty stores" Modern Acarology, Eds. Dusabeck & Bukva, vol. 1, pp. 607-610 (1991).

Zdarkova et al., "Space requirements of *Cheyletus eruditus* (Schrank) and *Cheyletus malaccensis*, Oudemans (Acarina, Cheyletidae)" Advances in Stored Product Protection, Eds. Credland, P.F. et al Proceedings of the VIII IWSCPP, pp. 183-185 (2002).

Zdarkova et al., "The effects of physical factors on survival of stored food mites" Exp. Appl. Acarol. 17:197-204 (1993).

Zdarkova et al., "Compatibility of *Cheyletus eruditus* (Schrank) (Arari: Cheyletidae) and *Cephalonomia tarsalis* (Ashmead) (Hymenoptera: Bethylidae) in Biological Control of Stored Grain Pests" Plant Protect. Sci. vol. 39, No. 1 pp. 29-34 (2003).

Zhang et al., "Potential of *amblyseius cucumeris* (Acari: phytoseiidae) as a biocontrol agent against *schizotetranychus nanjingensis* in Fujian, China" Systematic and Applied Acarology Special Publications vol. 4, pp. 109-124 (2000).

McKenzie et al., "Khishchye kleshchi v zakrytom grunte (Predatory mite under cover)" Kiev, Naukova Dumka, pp. 35 / Doss 13 EA: pp. 35, 128, 136-143 (1991).

Karg, W. "Progress in the use of predatory mites for biological control in greenhouses. Fortschritte bei der Anwendung von Raubmilben zur biologischen Schädlingsbekämpfung in Gewächshäusern" Gartenbau: Zeitschrift fuer den Gemuesebau, Obstbau and Zierpflanzenbau der D.D.R. Voortz. Van : Deutsche Gartenbau Voortg. Als Gartenbau, vol. 36, No. 2 pp. 44-46 (1989).

Karg et al., "Advantages of oligophagous predatory mites for biological control" Institute of plant protection Kleinmachnow, near Berlin GDR (1987).

\* cited by examiner

Figure 1

List of phytoseiid species and their genus name as referred in : Moraes, G.J. de, J.A. McMurtry, H.A. Denmark & C.B. Campos (2004). A revised catalog of the mite family Phytoseiidae. Magnolia Press Auckland New Zealand 494 pp.

Family : PHYTOSEIIDAE Berlese
    Subfamily : AMBLYSEIINAE Muma
        Genus : Amblyseius Berlese
            Amblyseius andersoni (Chant, 1957)
            Amblyseius swirskii Athias-Henriot, 1962, (Chant and McMurtry), 2004, (= Typhlodromips swirskii (Athias-Henriot), 1962, Moraes et al., 2004)
            Amblyseius largoensis (Muma, 1955)
        Genus : Euseius Wainstein
            Euseius finlandicus (Oudemans, 1915)
            Euseius hibisci (Chant, 1959)
            Euseius ovalis (Evans, 1953)
            Euseius victoriensis (Womersley, 1954)
            Euseius stipulatus ((Athias-Henriot, 1960)
            Euseius scutalis (Athias-Henriot, 1958)
            Euseius tularensis Congdon
            Euseius addoensis (van der Merwe & Ryke, 1964)
            Euseius citri (van der Merwe & Ryke, 1964)
        Genus : Neoseiulus Hughes
            Neoseiulus barkeri Hughes, 1948
            Neoseiulus californicus (McGregor, 1954)
            Neoseiulus cucumeris (Oudemans, 1930)

Fig 1 continued

Neoseiulus longispinosus (Evans, 1952)
        Neoseiulus womersleyi (Schicha, 1975)
        Neoseiulus idaeus Denmark & Muma, 1973
        Neoseiulus fallacis (Garman, 1948)

Genus : Typhlodromalus Muma
        Typhlodromalus limonicus (Garman & McGregor, 1956)
        Typhlodromalus peregrinus (Muma, 1955a)

Genus : Typhlodromips De Leon
        Typhlodromips montdorensis (Schicha, 1979)

Subfamily : TYPHLODROMINAE Scheuten
    Genus : Galendromus Muma
        Galendromus occidentalis (Nesbitt, 1951)

Genus : Typhlodromus Scheuten
        Typhlodromus pyri Scheuten, 1857
        Typhlodromus doreenae Schicha, 1987
        Typhlodromus athiasae Porath & Swirski, 1965

MITE COMPOSITION, USE THEREOF, METHOD FOR REARING A PHYTOSEIID PREDATORY MITE, REARING SYSTEM FOR REARING SAID PHYTOSEIID PREDATORY MITE AND METHODS FOR BIOLOGICAL PEST CONTROL ON A CROP

This invention according to a first aspect relates to a novel mite composition.

According to a second aspect the invention relates to a novel method for rearing a phytoseiid predatory mite species.

According to a third aspect the invention relates to a novel use of the Astigmatid mite species *Carpoglyphus lactis* as a factitious host, for rearing a phytoseiid predatory mite species.

According to a fourth and fifth aspect the invention relates to a novel rearing system for rearing a phytoseiid predatory mite species and to the use of this rearing system for the control of crop pests.

According to yet further aspects the invention relates to a method for biological pest control in a crop employing the mite composition according to the invention.

In the following description and claims the names of the phytoseiid mites is as referred to in de Moraes, G. J. et al., 2004, unless otherwise stated. An overview of the referenced families and species is provided in FIG. 1.

Phytoseiid predatory mites (Phytoseiidae) are widely used for biological control of spider mites and *thrips* in greenhouse crops. The most important *thrips* species in greenhouse crops are Western Flower *Thrips* (*Frankliniella occidentalis*) and Onion *Thrips* (*Thrips tabaci*). They can be controlled with the predatory mites *Amnblyseius cucumeris* and *Amblyseius barkeri* (Hansen, L. S. and Geyti, J., 1985; Ramakers, P. M. J. and van Lieburg, M. J., 1982; Ramakers, P. M. J., 1989; Sampson, C., 1998; and Jacobson, R. J., 1995) and *Iphiseius degenerans* (Ramakers, P. M. J. and Voet, S. J. P., 1996). In the absence of prey these species are able to establish and maintain in crops which provide a continuous supply of pollen, such as sweet peppers (*Capsicum annuum* L.). In crops where pollen is not freely available, such as for example cucumbers and most ornamental crops, these species cannot be used unless food is artificially provided. This can be done by dusting plant pollen on the crop.

Alternatively a controlled release rearing system (as disclosed by Sampson, C. (1998) or in GB2393890) can be used for *Amblyseius cucumeris*. This controlled release rearing system consists of a sachet with a compartment which contains a food mixture, consisting of bran, yeast and wheat germ; a population of the grain mite *Tyrophagus putrescentiae* and a population of the predatory mite *Amblyseius cucumeris*. The grain mite *Tyrophagus putrescentiae* will develop an active population on the food mixture and serves as a factitious host for the predatory mite population. The sachets are hung in the crop by means of a hook and will continuously release predatory mites over a period of 4 to 6 weeks.

Because *Amblyseius cucumeris* has a rather weak numerical response to the presence of food, large quantities of predatory mites have to be released into a crop in order to have sufficient pest control. This is economically possible because *Amblyseius cucumeris* can be economically reared in very large quantities on the grain mite *Tyrophagus putrescentiae*, which may be reared in sufficient amounts on the above described food mixture.

Although there are much more efficient predatory mites for *thrips* control with a higher predation rate and numerical response, such as *Typhlodromalus limonicus* and *Iphiseius degenerans*, *Amblyseius cucumeris* is still the most commonly used species because it can easily be reared in very large quantities.

*Iphiseius degenerans* is mass-reared on Castor Bean Plants (*Ricinus communis* L., Euphorbiaceae) which provide a continuous supply of pollen on which the mites can develop large populations. Because of the large surface and high investment in greenhouses needed for growing the plants, the cost price of *Iphiseius degerenans* is very high compared to *Amblyseius cucumeris*. Due to this high cost price growers can only release very low numbers, typically 1000-2000 predatory mites per hectare. Therefore, the application of *Iphiseius degenerans* is limited to peppers (*Capsicum annuum* L.), which provide sufficient pollen on which the predatory mites can develop a population, which is sufficient for pest control. It may take several months before the population of *Iphiseius degenerans* is at full strength in a crop in order to be able to have a significant impact on *thrips* pest populations.

Two-spotted Spider Mites (*Tetranychus urticae*) are successfully controlled in greenhouse and outdoor crops worldwide by releasing predatory mites. The most important species are *Phytoseiulus persimilis* (Hussey., N. W. and Scopes, N. E. A., 1985), which is the oldest mite which is commercially available for biological control and *Neoseiulus californicus* (Wei-Lan Ma and Laing, J. E., 1973). Both predatory mites are mass-reared on their natural host *Tetranychus urticae* on bean plants (Phaseolus vulgaris) in greenhouses. Castagnoli, M. and Simoni, S. (1999) have also described a method for mass-rearing *Neoseiulus californicus* on the House Dust Mite *Dermatophagoides farinae*. However, house Dust Mites (*Dermatophagoides farinae* and *Derinatophagoides pteronyssinus*) produce important allergens, implicated in allergic asthma, rhinitis, conjunctivitis and dermatitis. Therefore their use in controlled release rearing systems for releasing predatory mites in crops has disadvantages. Another disadvantage is that when House Dust Mites are used for mass-rearing purposes, extensive measures are advisable and in certain cases necessary for worker protection.

Scientific literature reports several predatory mites which prey on whiteflies (Teich, Y. 1966; Swirski, E. et al., 1967; Nomikou, M. et al., 2001). Unfortunately, to date there are still no predatory mites commercially available for biological control of whiteflies. Probably because despite the known predation of predatory mites on whiteflies their usability as augmentative biological control agents against whiteflies has not been recognized in the art. In augmentative biological control, biological agents are released in a crop for the control of a pest. Even more important, no economic mass-rearing systems, necessary for allowing the release of large numbers of the predatory mites into a crop, which is of utmost importance for their usability as an augmentative biological control agent, are available in the art for those predatory mite species which could potentially be efficacious against white flies.

Instead whiteflies are controlled by releasing parasitoid wasps such as *Encarsia formosa* and *Eretmocerus eremicus* against the Greenhouse Whitefly *Trialeurodes vaporariorum* and the parasitoid wasp *Eretmocerus mundus* against the Tobacco Whitefly *Bemisia tabaci*. Also several predators are mass-reared and released, such as for example the predatory Mirid bug *Macrolophus caliginosus* and the coccinellid *Delphastus catalinae*. Mass-rearing of all these parasitoids and predators involves the greenhouse production of plants and whiteflies which involves considerable investments.

Biological control of whiteflies and other crop pests with predatory mites which can be economically reared in large quantities on a factitious host mite in a rearing medium would be very advantageous because such a rearing system uses a limited surface. Furthermore in such a system rearing of the predatory mite can be performed in controlled climate rooms. As such it does not require large investments in greenhouses and crops.

Recent research has indicated the potential of the predatory mite *Amblyseius swirskii* as a very efficient biological control agent of thrips (*Thrips tabaci* and *Frankliniella occidentalis*) and whiteflies (*Trialeurodes vaporariorum* and *Bemisia tabaci*) (Nomikou, M., Janssen, A., Schraag, R. and Sabelis, M. W., 2001; Messelink, G. & Steenpaal, S. 2003; Messelink, G. 2004; Messelink, G. & Steenpaal, S. 2004; Bolckmans, K. & Moerman, M. 2004; Messelink, G. & Pijnakker, J. 2004). *Amblyseius swirskii* has shown a very strong numerical response to the presence of pests and plant pollen. This means that, compared to *Amblyseius cucumeris*, much lower numbers of mites have to be released in order to acquire good biological control. In one trial, release of 1 *Amblyseius swirskii* per leaf on sweet pepper plants resulted in the same level of control of Western Flower Thrips as releasing 30 *Amblyseius cucumeris* per leaf (Bolckmans, K. & Moerman, M. 2004).

The prior art describes rearing of *Amblyseius cucumeris* and *Amblyseius barkeri* with the aid of a factitious host mite species from the genus *Tyrophagus*, in particular *Tyrophagus putrescentiae, Tyrophagus tropicus, Tyrophagus casei* (Sampson, C., 1998; Jacobson, R. J., 1995; Bennison, J. A. and R. Jacobson, 1991; Karg et al., 1987; and GB293890) and from the genus Acarus, in particular *Acarus siro* (Beglyarov et al., 1990) and *Acarus farris* (Hansen, L. S. and J. Geyti, 1985; Ramakers, P. M. J. and van Lieburg, M. J., 1982), which all belong to the family of the Acaridea.

The most common rearing host for *Amblyseius cucumeris* is *Tyrophagus putrescentiae*. An important disadvantage of *Tyrophagus putrescentiae* is that it can cause plant damage to young plant leaves when it is present on crops, e.g. when used as a factitious host in slow release breeding sachets similar to that disclosed by (Sampson, C., 1998) or in GB293890. This is especially the case in cucumber crops during periods of high humidity especially if this is combined with a low light intensity.

Castagnoli et al. have also described the possibility of mass-rearing. *Neoseiulus californicus* (Castagnoli, M. and S. Simoni, 1999) and *Amblyseius cucumeris* (Castagnoli, M., 1989) on the House Dust Mite *Dermatophagoides farinae* as a factitious rearing host. However, House Dust Mites (*Dermatophagoides farinae* and *Dermatophagoides pteronyssinus*) produce important allergens, implicated in allergic asthma, rhinitis, conjunctivitis and dermatitis.

Thus there is a need in the art for additional factitious hosts which can be used for mass rearing beneficial mites, such as predatory mites. Especially for rearing of *Amblyseius swirskii*. For this predatory mite rearing has only been disclosed in the art using pollen (Messelink, G. & Pijnakker, J. 2004) or eggs from the lepidopterans *Corcyra cephalonica* or *Ephestia kuehniella* (Romeih, A. H. M. et al., 2004).

Rearing on pollen necessitates either large greenhouse areas for the production of plants such as Castor Bean Plants (*Ricinus communis*) to obtain sufficient pollen, or collecting suitable plant pollen such as from Cattail (*Typha* spp.) outdoors. Collecting plant pollen outdoors is very labour intensive and only limited quantities can be collected. Honeybee collected plant pollen is unsuitable for rearing predatory mites.

Rearing on lepidopteran eggs requires large investments in production facilities and thus is very expensive.

In view of the above there is a need in the art for alternative factitious host mites, which can be employed in the mass-rearing of phytoseiid predatory mites.

It has now been found that Astigmatid mite species from the family of the Carpoglyphydae may be used as factitious host for a great number of phytoseiid predatory mite species.

Thus according to a first aspect the invention relates to a mite composition comprising a rearing population of a phytoseiid predatory mite species and a factitious host population comprising at least one species selected from the family of the Carpoglyphidae such as from the genus *Carpoglyphus*, preferably the Dried Fruit Mite *Carpoglyphus lactis* (Linne, 1758) (Acari: Carpoglyphidae).

The phytoseiid predatory mite species which are most likely to be able to feed on Carpoglyphidae and in particular *Carpoglyphus lactis* are oligophagous phytoseiid predatory mite species. An oligophagous phytoseiid predatory mite species is a phytoseiid predatory mite species which is able to use at least a few different prey species as a food source for its development (growth and reproduction). As such the term oligophagous predatory mite species in this specification includes a polyphagous mite species, being a predatory mite which can use a great number of prey species as a food source for its development. Thus the term oligophagous predatory mite species is to be understood to mean a non-monophagous predatory mite species.

A factitious host species is a species which inhabits a different natural habitat then the phytoseiid predatory mite, but nevertheless one or more life stages of the factitious host are suitable prey for at least one life stage of the phytoseiid predatory mite. Most importantly the phytoseiid predatory mite has the ability to develop and to reproduce when feeding upon a diet of the factitious host such that the number of individuals in the rearing population can grow.

Phytoseiid predatory mites have their natural habitat on plants where they prey on pest organisms (insects and mites). They may be isolated from their natural habitats as described by de Moraes et al., 2004.

Carpoglyphidae are described by Hughes, A. M. (1977). Based on the disclosure of this document the skilled person will be able to isolate specific species from this family from their natural habitat. *Carpoglyphus lactis* is a cosmopolitan species which develops on and in a variety of stored organic materials. It is mainly found on dried fruit, such as dried figs, prunes, raisins, etcetera and on the debris in honeybee hives (Hughes, A. M. 1977; Chmielewski; W., 1971 (a); Chmielewski, W., 1971 (b)).

Thus the composition according to the invention provides a new association of mites, which does not occur naturally, as the phytoseiid predatory mite inhabits a different habitat then the Carpoglyphidae.

The composition according to the invention is not only suitable for mass-rearing of a phytoseiid predatory mite. As it also comprises mobile preying life stages of a phytoseiid predatory mite, or life stages which can develop into these mobile life stages, it can also be employed as a biological crop protection agent.

In a preferred embodiment the composition comprises a carrier for the individuals of the populations. The carrier can be any solid material which is suitable to provide a carrier surface to the individuals. Preferably the carrier provides a porous medium, which allows exchanges of metabolic gases and heat produced by the mite populations. Examples of suitable carriers are plant materials such as (wheat) bran, buckwheat husks, rice husks, saw dust, corn cob grits etcetera.

It is further preferred if a food substance suitable for the factitious host population is added to the composition. Alternatively the carrier itself may comprise a suitable food substance. A suitable food substance may be similar to that described by Parkinson, C. L., 1992; Solomon, M. E. & Cunnington, A. M., 1963; Chmielewski, W, 1971 a; Chmielewski, W, 1971 b or GB2393890.

According to a preferred embodiment of the composition the phytoseiid predatory mite is selected from:

the subfamily of the Amblyseiinae, such as from the Genus *Amblyseius*, e.g. *Amblyseius andersoni*, *Amblyseius swirskii* or *Amblyseius largoensis*, from the genus *Euseius* e.g. *Euseius finlandicus*, *Euseius hibisci*, *Euseius ovalis*, *Euseius victoriensis*, *Euseius stipulatus*, *Euseius scutalis*, *Euseius tularensis*, *Euseius addoensis* or *Euseius citri*, from the genus *Neoseiulus* e.g. *Neoseiulus barkeri*, *Neoseiulus californicus*, *Neoseiulus cucumeris*, *Neoseiulus longispinosus*, *Neoseiulus womersleyi*, *Neoseiulus idaeus* or *Neoseiulus fallacies*, from the genus *Typhlodromalus* e.g. *Typhlodromalus limonicus* or *Typhlodromalus peregrinus* from the genus *Typhlodromips* e.g. *Typhlodromips montdorensis*;

the subfamily of the Typhlodrominae, such as from the genus *Galendroinus* e.g. *Galendroinus occidentalis*, from the genus *Typhlodromus* e.g. *Typhlodromus pyri*, *Typhlodromus doreenae* or *Typhlodromus athiasae*. These phytoseiid predatory mite species may be considered as being oligophagous predatory mite species.

The phytoseiid predatory mite preferably is selected as *Amblyseius swirskii* Athias-Henriot, 1962, (Chant and McMurtry), 2004, (=*Typhlodromips swirskii* (Athias-Henriot), 1962, De Moraes et al., 2004). For this species rearing on a factitious host mite has not been disclosed in the art. The present invention now for the first time discloses a mite composition which can be used for economic rearing of *Amblyseius swirskii* by using a species from the family of the Carpoglyphidae as a factitious host. Making it possible to use *Amblyseius swirskii* as an augmentative biological pest control agent. It should however be understood that in certain embodiments of the invention the phytoseiid predatory mite species is selected from a species other then *Amblyseius swirskii*.

Differences in acceptance of the factitious host may be observed between different strains of the phytoseiid predatory mite species. Furthermore, it might be possible to breed a strain which is adapted to a specific factitious host by selective breeding.

In this specification the term rearing must be understood to include the propagation and increase of a population by means of sexual reproduction.

A rearing population may comprise sexually mature adults from both sexes, and/or individuals of both sexes of other life stages, e.g. eggs and/or nymphs, which can mature to sexually mature adults. Alternative the rearing population may comprise one or more fertilized females. In essence the rearing population is capable of increasing the number of its individuals by means of sexual reproduction.

Preferably the factitious host population is a rearing population, as defined above, such that it may sustain or even develop itself to a certain degree. If the factitious host is provided as a rearing population, preferably a food substance for the factitious host is also provided. The food substance may be similar to a food substance as disclosed in Solomon, M. E. and Cunnington, A. M., 1963; Parkinson, C. L., 1992; Ramakers, P. M. J. and van Lieburg, M. J., 1982; GB2393890.

The factitious host is preferably selected as *Carpoglyphus lactis*. *Carpoglyphus lactis* also called the dried fruit mite is a cosmopolitan species which develops on and in a variety of stored organic materials. It is mainly found on dried fruit, such as dried figs, prunes, raisins, etcetera and on the debris in honeybee hives (Hughes, A. M., 1977; Chmielewski, W., 1971 (a); Chmielewski, W., 1971 (b)). Contrary to *Tyrophagus putrescentiae*, *Carpoglyphus lactis* does not cause damage to crops. Therefore, a factitious host from this preferred selection will have benefits when the composition according to the invention is used for crop protection in such a way that individuals of the factitious host population may come in contact with the crop e.g. when applied directly on or in the vicinity of the crop or when used in slow/controlled/sustained release sachets.

A further benefit of *Carpoglyphus lactis* is that it is considered to be a cosmopolitan species. As such international trade of products comprising it will encounter less regulatory restrictions as is encountered in many countries for foreign species.

Also it has been found that *Carpoglyphus lactis* is in particular a suitable factitious host for *Amblyseius swirskii* as this predator can feed on multiple life stages and under certain circumstances all life stages of this host.

In the composition the number of individuals of the phytoseiid predatory mite species relative to the number of individuals of the factitious host may be from about 1000:1 to 1:20, such as about 100:1 to 1:20 e.g. 1:1 to 1:10, preferably about 1:4, 1:5 or 1:7.

The relative numbers may depend on the specific intended use of the composition and/or the stage of development of phytoseiid mite population on the factitious host. In general compositions wherein individuals of the factitious host are present in excess to the individuals of the phytoseiid mite are preferred for rearing of the phytoseiid mite species, so that sufficient prey is provided to the phytoseiid mite. However, as the phytoseiid mite population will increase while preying on the factitious host, the relative number of individuals of the phytoseiid mite species will increase.

A composition comprising a high relative numbers of the phytoseiid predatory mite may be formed from a composition comprising a smaller relative number and allowing the rearing population of the phytoseiid predatory mite to develop by preying on the factitious host. Alternatively a composition comprising a small relative number of the phytoseiid predatory mite can be formed by mixing a composition comprising a higher relative number with a composition comprising a smaller relative number, including a composition comprising solely the factitious host, optionally in combination with the carrier and/or a food substance suitable for the factitious host.

According to a further aspect the present invention relates to a method for rearing the phytoseiid predatory mite species. The method comprises providing a composition according to the invention and allowing individuals of said phytoseiid predatory mite to prey on individuals of said factitious host population.

For an optimal development of the phytoseiid predatory mite, the composition is e.g. maintained at 18-35° C., preferably 20-30° C., more preferably 20-25° C., most preferably 22-25° C. Suitable relative humidity ranges are between 75-95%, preferably 80-90%. These temperature and relative humidity intervals are in general also suitable to maintain the factitious host species.

It is preferred that the composition comprises a carrier which can provide a porous medium and a food substance for the factitious host specie and that the factitious host species is maintained as a three dimensional culture on the carrier. In such a three dimensional culture members of the factitious host species are free to move in three dimensions. In this way they may infest a larger volume of the carrier and utilise the food substance more optimally. Considering the size of the mobile stages of the phytoseiid predatory mite species relative to individuals of the factitious host, this organism will in general also infest the total volume of the carrier, when foraging for the factitious host. Preferably the three dimensional culture is obtained by providing the carrier in a three dimensional layer, i.e. a layer having three dimensions, of which two dimensions are larger then one dimension. Exemplary is a horizontal layer with a length and breadth in the order of metres and a certain thickness in the order of centimetres. A three dimensional layer is preferred because it will allow sufficient exchange of metabolic heat and gasses and will provide a larger production volume compared to a two dimensional layer.

According to a further aspect the invention is aimed to the use of an Astigmatid mite selected from the family of the Carpoglyphidae such as from the genus *Carpoglyphus*, preferably the species *Carpoglyphus lactis*, as a factitious host for rearing a phytoseiid predatory mite.

The Astigmatid mite is preferably selected from the genus *Carpoglyphus* and most preferably is *Carpoglyphus lactis*, for reasons discussed above.

The phytoseiid predatory mite is preferably selected from:
  the subfamily of the Amblyseiinae, such as from the Genus *Amblyseius*, e.g. *Amblyseius andersoni*, *Amblyseius swirskii* or *Amblyseius largoensis*, from the genus *Euseius* e.g. *Euseius finlandicus*, *Euseius hibisci*, *Euseius ovalis*, *Euseius victoriensis*, *Euseius stipulatus*, *Euseius scutalis*, *Euseius tularensis*, *Euseius addoensis* or *Euseius citri*, from the genus *Neoseiulus* e.g. *Neoseiulus barkeri*, *Neoseiulus californicus*, *Neoseiulus cucumeris*, *Neoseiulus longispinosus*, *Neoseiulus womersleyi*, *Neoseiulus idaeus* or *Neoseiulus fallacies*, from the genus *Typhlodromalus* e.g. *Typhlodromalus limonicus* or *Typhlodromalus peregrinus* from the genus *Typhlodromips* e.g. *Typhlodromips montdorensis*;
  the subfamily of the Typhlodrominae, such as from the genus *Galendromus* e.g. *Galendromus occidentalis*, from the genus *Typhlodromus* e.g. *Typhlodromus pyri*, *Typhlodromus doreenae* or *Typhlodromus athiasae*.

According to a further aspect the invention relates to a rearing system for rearing the phytoseiid predatory mite.

The rearing system comprises a container holding the composition according to the invention. The container may be of any type which is suitable for restraining individuals of both populations. The rearing system may comprise means which facilitate exchange of metabolic gases and heat between it's interior and it's exterior such as ventilation holes. Such ventilation holes must not allow the escape of individuals of the populations from the container. This can be effected by covering the ventilation holes e.g. with a mesh.

The rearing system may be suitable for mass-rearing the phytoseiid mite species. Alternatively the rearing system may also be used for releasing the phytoseiid predatory mite in a crop. In this case it is preferred that the container can be rendered suitable to release mobile stages of the phytoseiid predatory mite at a certain moment. This can be effected by providing a closed opening in the container which can be opened. Alternatively or in combination therewith a relatively small releasing opening may be provided in the container, such that the number of phytoseiid mobile stages which leave the container in a given time interval is restricted. In this way the rearing system may function similar to the slow release or sustained release system as disclosed by Sampson, C., 1998 and in GB2393890.

In such a rearing system for releasing the phytoseiid predatory mite in a crop the container is preferably dimensioned such that it can be hung in the crop or placed at the basis of the crop. For hanging in the crop the container may be provided with hanging means, such as a cord or a hook.

According to a further aspect the invention is aimed at the use of the composition or the rearing system for controlling crop pests in a commercial crop.

The pest may be selected from, white flies, such as *Trialeurodes vaporariorum* or *Bemisia tabaci; thrips*, such as *Thrips tabaci* or *Frankliniella* spp., such as *Frankliniella Occidentalis*, spider mites such as *Tetranychus urticae*, tarsonemid mites such as Polyphagotarsonemus latus. The phytoseiid predatory mite *Amblyseius swirskii* has shown a good efficacy for controlling these pests The crop may be selected from, but is not restricted to (greenhouse) vegetable crops such as peppers (*Capsicum annum*, eggplants (*Solanum melongena*), Curcubits (Cucurbitaceae) such as cucumbers (*Cucumis sativa*), melons (*Cucumis melo*), watermelons (*Citrullus lanatus*); soft fruit (such as strawberries (*Fragaria x ananassa*), raspberries (*Rubus ideaus*)), (greenhouse) ornamental crops (such as roses, gerberas, chrysanthemums) or tree crops such as Citrus spp.

The invention further relates to a method for biological pest control in a crop comprising providing a composition according to the invention to said crop.

The pest may be selected similarly as in the use according to the invention.

In the method according to the invention the composition may be provided by applying an amount of said composition in the vicinity, such as on or at the basis of a number of crop plants. The composition may be provided to the crop plant simply by spreading it on the crop plant or at the basis of the crop plant as is common practice for employing predatory mite compositions for augmentative biological pest control. The amount of the composition which may be provided to each individual crop plant by way of spreading may range from 1-20 ml such as 1-10 ml, preferably 2-5 ml.

Alternatively the composition may be provided to the number of crop plants in the rearing system according to the invention which is suitable for releasing the phytoseiid predatory mite in a crop. The rearing system may be placed in the vicinity, such as in or at the basis, of a number of crop plants.

In the method for biological pest control according to the invention it may not be necessary to provide the composition to all crop plants. As commercial crops are normally densely cultivated. The phytoseiid predatory mites may spread from one crop plant to another. The number of crop plants which must be provided with the composition according to the invention in order to provide sufficient crop protection may depend on the specific circumstances and can be easily determined by the skilled person based on his experience in the field. Usually the number of phytoseiid predatory mites released per hectare is more determining. This number may range from 1000-4 million per hectare, typically 100.000-1 million or 50.000-500.000 per hectare.

In a further preferred embodiment of the method for biological pest control according to the invention the crop is selected as described in relation to the use of the composition.

The invention will now be further described with reference to the following examples, which show non-limiting embodiments of different aspects of the invention.

EXAMPLE 1

Mass-rearing of the Astigmatid Mite *Carpoglyphus lactis*.

*Carpoglyphus lactis* was mass-reared on a medium containing baker's yeast (Chmielewski, W., 1971 (a); Chmielewski, W., 1971 (b)).

The culture is kept in ventilated containers (for example buckets with sufficient ventilation holes with 47 micron gauze to prevent the mites from escaping) at between 22° and 25° C. and a relative humidity of 85 to 90%. Successful mass-rearing may be effected by adding fresh medium at least once every week. The amount depends on the number of mites in the medium but typically between 100 to 300% of medium of the original volume of the culture is added. The thickness of the rearing layer can be 1 to 10 cm, but not too thick to ensure optimal exchange of metabolic gases such as carbon dioxide and oxygen and metabolic heat. Biomass weight percentages of mites to medium between 20% and 30% were reached when *Carpoglyphus lactis* was reared on this medium. Typically the population will increase 2 to 4 times each week.

EXAMPLE 2

Mass Rearing of *Amblyseius swirskii* on *Carpoglyphus lactis*

*Amblyseius swirskii* is reared in ventilated containers (for example buckets with sufficient ventilation holes to ensure optimal exchange of metabolic gases and heat with 47 micron gauze to prevent the mites from escaping) with a layer of 5 to 25 cm of buckwheat husks as a carrier.

The carrier layer should not be too thick to ensure optimal exchange of metabolic gases such carbon dioxide and oxygen and metabolic heat. At least once every week a rearing population of *Carpoglyphus lactis* with a biomass weight percentages of mites to medium of 15% to 30% is added to the container.

The quantity of *Carpoglyphus lactis* to be added is calculated based on the number of the phytoseiid predatory mites and *Carpoglyphus lactis* present in the rearing container. Optimally after adding fresh *Carpoglyphus lactis* the ratio of predators to prey should be between 1:7 to 1:12. The culture is kept at a temperature between 22° and 25° C., a relative humidity of 85 to 90% and a CO2 level of maximum 750 ppm in the rearing container. In this way a rearing population of *Amblyseius swirskii* can double to triple each week. Typically densities of 100 to 500 predatory mites per gram of rearing substrate can be achieved.

EXAMPLE 3

Oviposition Test of *Amblyseius swirskii* on Juvenile and Adult Life Stages of *Carpoglyphus lactis*.

The objective of this experiment is to investigate if *Amblyseius swirskii* has a preference for juvenile stages (eggs, larvae and nymphs) of *Carpoglyphus lactis* or that it can also feed on adult life stages of this factitious host. For this different rearing systems of *Amblyseius swirskii* (some of them fed with juvenile stages of *Carpoglyphus lactis* and others fed with adults of *Carpoglyphus lactis*) were created. The differences between the mean number of eggs laid per *Amblyseius swirskii* female per day in the case that the food source are adult stages of *Carpoglyphus lactis* is compared to the case wherein the food source are juvenile stages of *Carpoglyphus lactis*.

Material and Methods

At the beginning of the experiment the *Amblyseius swirskii* adults were taken from an *Amblyseius swirskii* mass-culture which was started a few weeks earlier. 30 young adult females and 12 males were picked up from this mass-culture and transferred to six freshly prepared rearing containers. 5 females and 2 males of *Amblyseius swirskii* were placed in each one. In three of them as a food source was placed an ample amount of juvenile stages of *Carpoglyphus lactis*. The remaining three test cultures were fed with adults of *Carpoglyphus lactis*.

Once the six test cultures were prepared, they were located in a climate room under controlled temperature (25° C.) and humidity (75%) conditions. After two or three days in these conditions, they were taken out. Six new rearing containers, similar to the previous ones, were prepared to transfer the same 5 females and 2 males previously used. Ample amount of juvenile or adult stages of *Carpoglyphus lactis* as a food source were added to each test container as in the previous step. After transferring the males and females, the number of eggs was counted in the rearing containers from which they were transferred.

The old rearing systems were conserved in the climate room during two or three days for a second counting in order to detect some possible hidden offspring, after which they were destroyed. Similar to the old rearing systems, the new ones were also maintained to repeat the same procedure. Every day the residual amount of *Carpoglyphus lactis* in each rearing container was checked. If necessary a sufficient amount was added.

Every two or three days data were obtained by evaluating the number of offsprings of both the new rearing (first counting) and the old one (second counting). Based on the number of females and on the total amount of offspring which was found on each rearing container, the mean number of eggs laid per female per day was obtained.

Results

Adult Stages of *Carpoglyphus lactis* as a Food Source

When comparing the evolution of the number of eggs laid per female during the total experiment (making one assessment each 2-3 days), the mean ranges from 1.27 to 2.07 eggs/female/day.

For the whole period, the general mean is 1.80 eggs per female per day. The total amount of eggs laid per female is about 29 over a 16 days period. Comparing the mean number of eggs laid per female per day for the first, second and third independent rearing container, these are 1.84, 1.72 and 1.85, respectively. The experimental data is presented in table 1 below.

TABLE 1

Food source: adults of *Carpoglyphus lactis*. Data of the mean number of eggs laid per *Amblyseius swirskii* female per day for the 3 independent rearing systems and for the global experiment.

| Exp. | Date | Females | Total offspring | egg/day/ female | Mean eggs/day/ female |
|---|---|---|---|---|---|
| 1 | 10/11 | 5 | 15 | 1.50 | 1.84 |
|  | 15/11 | 5 | 24 | 1.60 |  |
|  | 17/11 | 5 | 17 | 1.70 |  |
|  | 19/11 | 5 | 23 | 2.30 |  |
|  | 22/11 | 5 | 30 | 2.00 |  |
|  | 24/11 | 5 | 17 | 1.70 |  |
|  | 26/11 | 5 | 21 | 2.10 |  |
| 2 | 10/11 | 5 | 10 | 1.00 | 1.72 |
|  | 15/11 | 5 | 31 | 2.07 |  |
|  | 17/11 | 5 | 20 | 2.00 |  |

TABLE 1-continued

Food source: adults of *Carpoglyphus lactis*. Data of
the mean number of eggs laid per *Amblyseius swirskii* female
per day for the 3 independent rearing systems and for the
global experiment.

|   | 19/11 | 5 | 21 | 2.10 |      |
|---|-------|---|----|------|------|
|   | 22/11 | 5 | 31 | 2.07 |      |
|   | 24/11 | 5 | 13 | 1.30 |      |
|   | 26/11 | 5 | 15 | 1.50 |      |
| 3 | 10/11 | 5 | 13 | 1.30 | 1.85 |
|   | 15/11 | 5 | 34 | 2.27 |      |
|   | 17/11 | 5 | 23 | 2.30 |      |
|   | 19/11 | 5 | 18 | 1.80 |      |
|   | 22/11 | 5 | 25 | 1.67 |      |
|   | 24/11 | 5 | 19 | 2.38 |      |
|   | 26/11 | 5 | 10 | 1.25 |      |

| Day | Period | Females | Offspring | eggs/day/ female | Mean eggs/day/ female |
|-----|--------|---------|-----------|------------------|------------------------|
| 10/11 | 0-2 days | 15 | 38 | 1.27 | 1.80 |
| 15/11 | 3-5 days | 15 | 89 | 1.98 |      |
| 17/11 | 6-7 days | 15 | 60 | 2.00 |      |
| 19/11 | 8-9 days | 15 | 62 | 2.07 |      |
| 22/11 | 10-12 days | 15 | 86 | 1.91 |      |
| 24/11 | 13-14 days | 14 | 49 | 1.75 |      |
| 26/11 | 15-16 days | 14 | 46 | 1.64 |      |

Juvenile Stages of *Carpoglyphus lactis* as a Food Source

If we compare the evolution of the number of eggs laid per female during the total experiment (making one assessment each 2-3 days), it was found that the mean ranges from 1.43 to 2.07 eggs/female/day.

For the whole period, the mean is 1.84 eggs per female per day. The total amount of eggs laid per female is about 33 over a 18 days period. Comparing the mean number of eggs laid per female per day for the 3 independent rearing containers, the means for the first, second and third rearing systems are 1.72, 1.89 and 1.81, respectively. The results are shown in table 2 below.

TABLE 2

Food source: juvenile stages of *Carpoglyphus lactis*.
Data of the mean number of eggs laid per *Amblyseius swirskii*
female per day for the 3 independent rearing systems and for
the global experiment.

| Exp. | Day | Females | Total offspring | egg/day/ female | Mean eggs/day/ female |
|------|-----|---------|-----------------|-----------------|------------------------|
| 1 | 10/11 | 5 | 18 | 1.80 | 172 |
|   | 12/11 | 5 | 21 | 2.10 |     |
|   | 15/11 | 5 | 31 | 2.07 |     |
|   | 17/11 | 5 | 17 | 1.70 |     |
|   | 19/11 | 5 | 16 | 1.60 |     |
|   | 22/11 | 5 | 33 | 2.20 |     |
|   | 24/11 | 4 | 10 | 1.25 |     |
|   | 26/11 | 4 | 8  | 1.00 |     |
| 2 | 10/11 | 6 | 15 | 1.25 | 1.89 |
|   | 12/11 | 6 | 24 | 2.00 |     |
|   | 15/11 | 6 | 31 | 1.72 |     |
|   | 17/11 | 6 | 25 | 2.08 |     |
|   | 19/11 | 6 | 26 | 2.17 |     |
|   | 22/11 | 6 | 36 | 2.00 |     |
|   | 24/11 | 6 | 25 | 2.08 |     |
|   | 26/11 | 6 | 22 | 1.83 |     |
| 3 | 10/11 | 5 | 20 | 2.00 | 1.81 |
|   | 12/11 | 5 | 21 | 2.10 |     |
|   | 15/11 | 5 | 26 | 1.73 |     |
|   | 17/11 | 5 | 21 | 2.10 |     |
|   | 19/11 | 4 | 17 | 1.70 |     |

TABLE 2-continued

Food source: juvenile stages of *Carpoglyphus lactis*.
Data of the mean number of eggs laid per *Amblyseius swirskii*
female per day for the 3 independent rearing systems and for
the global experiment.

|   | 22/11 | 4 | 24 | 2.00 |
|---|-------|---|----|------|
|   | 24/11 | 4 | 13 | 1.63 |
|   | 26/11 | 4 | 10 | 1.25 |

| Day | Period | Females | Offspring | eggs/day/ female | Mean eggs/day/ female |
|-----|--------|---------|-----------|------------------|------------------------|
| 10/11 | 0-2 days | 16 | 53 | 1.66 | 1.84 |
| 12/11 | 3-4 days | 16 | 66 | 2.06 |      |
| 15/11 | 5-7 days | 16 | 88 | 1.83 |      |
| 17/11 | 8-9 days | 16 | 63 | 1.97 |      |
| 19/11 | 10-12 days | 15 | 59 | 1.97 |    |
| 22/11 | 13-14 days | 15 | 93 | 2.07 |    |
| 24/11 | 15-16 days | 14 | 48 | 1.71 |    |
| 26/11 | 17-18 days | 14 | 40 | 1.43 |    |

The results show that *Amblyseius swirskii* can reproduce on both juvenile and adult stages of *Carpoglyphus lactis*.

EXAMPLE 4

Oviposition of *Amblyseius cucumeris* on *Carpoglyphus lactis*.

With the same general experimental outline as described in example 3, the mean number of eggs layed per *Amblyseius cucumeris* female when using *Carpoglyphus lactis* as a food source was determined.

In this experiment however, no discriminatory determinations for juvenile and adults of the factitious host were done. Instead individuals of the *Carpoglyphus lactis* population were added non-selectively.

Results

If we compare the evolution of the number of eggs laid per female in the total experiment (making one assessment each 2-3 days), we appreciate that, avoiding the first period (2 days) where the average is 1.72 eggs/female/day, in the 5 next periods the mean ranges from 2.17 to 2.31 eggs/female/day. For the whole period, the general mean is 2.13 eggs/female/day. The data are presented in table 3 below.

TABLE 3

Data for the mean number of eggs laid per female per
day for the 3 independent rearing systems and for the global
experiment.

| Exp. | Day | Females | Total offspring | egg/day/ female | Mean eggs/day/ female |
|------|-----|---------|-----------------|-----------------|------------------------|
| 1 | 29/10 | 5 | 19 | 1.90 | 2.32 |
|   | 01/11 | 5 | 37 | 2.47 |      |
|   | 05/11 | 5 | 26 | 2.60 |      |
|   | 08/11 | 5 | 35 | 2.33 |      |
|   | 10/11 | 5 | 24 | 2.40 |      |
|   | 12/11 | 5 | 22 | 2.20 |      |
| 2 | 29/10 | 5 | 25 | 2.50 | 2.39 |
|   | 01/11 | 5 | 37 | 2.47 |      |
|   | 05/11 | 5 | 25 | 2.50 |      |
|   | 08/11 | 5 | 36 | 2.40 |      |
|   | 10/11 | 5 | 19 | 1.90 |      |
|   | 12/11 | 5 | 26 | 2.60 |      |

TABLE 3-continued

Data for the mean number of eggs laid per female per day for the 3 independent rearing systems and for the global experiment.

| 3 | 29/10 | 6 | 11 | 0.92 | 2.13 |
|---|-------|---|----|------|------|
|   | 01/11 | 6 | 31 | 1.72 |      |
|   | 05/11 | 6 | 23 | 1.92 |      |
|   | 08/11 | 6 | 33 | 1.83 |      |
|   | 10/11 | 5 | 22 | 2.20 |      |
|   | 12/11 | 4 | 14 | 1.75 |      |

| Day | Period | Females | Offspring | eggs/day/female | Mean eggs/day/female |
|-----|--------|---------|-----------|-----------------|----------------------|
| 29/10 | 0-2 days | 16 | 55 | 1.72 | 2.13 |
| 01/11 | 3-5 days | 16 | 105 | 2.19 |  |
| 05/11 | 6-7 days | 16 | 74 | 2.31 |  |
| 08/11 | 8-10 days | 16 | 104 | 2.17 |  |
| 10/11 | 11-12 days | 15 | 65 | 2.17 |  |
| 12/11 | 13-14 days | 14 | 62 | 2.21 |  |

The results show that *Amblyseius cucumeris* is able to reproduce on *Carpoglyphus lactis*.

REFERENCE

Athias-Henriot, C. (1962) *Amblyseius swirskii*, un nouveau phytoseiide voisin d'A. andersoni (*Acariens anactinotriches*). Annales de l'Ecole Nationale d'Agriculture d'Alger, Algeria, 3, 1-7.

Beglyarov et al., 1990, Flour mite for mass breeding of phytoseiids, Zashchita-Rastenii, no. 10, pp 25. Bennison, J. A. and Jacobson, R., 1991, Integrated control of *Frankliniella occidentalis* (Pergande) in UK cucumber crops—evaluation of a controlled release system of introducing *Amblyseius cucumeris*, Med. Fac. Landbouww. Rijksuniv. Gent, 56/2a, pp 251-255.

Bolckmans, K. & Moerman, M. 2004, Nieuwe roofmijt verandert bestrijding in paprika. Groenten & Fruit 41: 24-25

Castagnoli, M., 1989, Biologia e prospettive di allevamento massale di *Amblyseius cucumeris* (Oud.) (Acarina: Pyroglyphidae) com preda.

Castagnoli, M. and Simoni, S., 1999, Effect of long-term feeding history on functional and numerical response of *Neoseiulus californicus* (Acari: Phytoseiidae), Experimental & Applied Acarology, 23, pp 217-234.

Castagnoli M., Simoni S. Biliotti N., 1999, Mass-rearing of *Amblyseius californicus* on two alternative food source—In: J. Bruin, L. P. S. van der Geest and M. W. Sabelis (eds), Ecology and Evolution of the Acari, Kluwer Acad, Publ., Dordrecht, The Nederlands, pp. 425-431.

Chant, D. A., and J. A., McMurtry, 2004, A review of the subfamily Amblyseiinae Muma (Acari: Phytoseiidae): Part III. The tribe Amblyseiini wainstein, subtribe Amblyseiina N. subtribe. Internat. J. Acarol., vol. 30, Nr. 3, p. 171-228.

Chmielewski, W., 1971 (a), Wyniki badan morfologicznych, biologicznych i ekologicznych nad roztoczkiem suszowym, *Carpoglyphus lactis* (L.) (The results of investigations on the morphology, biology and ecology of the dried-fruit mite, *Carpoglyphus lactis* (L.)), Prace-Naukowe-Instytutu-Ochrony-Roslin. 1971, publ. 1972, 13: 1, 87-106.

De Moraes, G. J., McMurtry, J. A., Denmark, H. A. & Campos, C. B., 2004. A revised catalog of the mite family Phytoseiidae. Magnolia Press Auckland New Zealand 494 pp.

Chmielewski, W., 1971 (b), Morfologia, biologia i ekologia *Carpoglyphus lactis* (L., 1758) (Glycyphagidae, Acarina) (The morphology, biology and ecology of *Carpoglyphus lactis* (L., 1758) (Glycyphagidae, Acarina)), Prace-Naukowe-Instytutu-Ochrony-Roslin. 1971, publ. 1972, 13: 2, 63-166.

Hansen, L. S. and Gevti. J., 1985, Possibilities and limitation of the use of *Amblyseius McKenziei* Sch. & Pr. for biological control of thrips (*Thrips tabaci* Lind.) On glasshouse corps of cucumber, Department of Zoology, Danish Research Centre for Plant Protection, Lyngby, Denmark, pp 145-150.

Hughes, A. M., 1977, The mites of stored food and houses. Ministry of Agriculture, Fisheries and Food, Technical Bulletin No. 9: 400 pp Hussey, N. W. and N. E. A. Scopes, 1985, Biological Pest Control: the Glasshouse Experience. Poole, UK.: Blandford Press (Ithaca, N.Y.: Cornell University Press)

Jacobson, R. J., 1995, Integrated pest management in cucumbers—prevention of establishment of *Frankliniella occidentalis* (Pergande), Med. Fac. Landbouww. Univ. Gent, 60/3a, pp 857-863.

Karg et al., 1987, Advantages of oligophagous predatory mites for biological control, Institute of Plant Protection Klenmachnow, pp 66-73.

Karg et al., 1989, Fortschritte bei der Anwendung von Raubmilben zur biologischen Schädlingsbekämpfung in Gewächshäusern, Gartenbau, 36, pp 44-46.

Karg. W., 1989, Die ökologische Differenzierung der Faubmilbarten der Überfamilie Phytoseiidea KARG (Acarina, Parasitiformes), Zool. Jb. Syst. 116, pp 31-46.

Messelink, G. & Steenpaal, S. 2003, Nieuwe roofmijten tegen trips in komkommer. Groenten & Fruit 43: 34-35.

Messelink, G. 2004, Nieuwe roofmijt wint met overmacht in komkommer. Groenten & Fruit 35: 22-23.

Messelink, G. & Pijnakker, J. 2004, Roofmijten bestrijden wittevlieg. Vakblad voor de Bloemisterij 43: 62.

Messelink, G. & Steenpaal, S. 2004, Roofmijt nu ook kaswittevlieg de baas. Groenten & Fruit 45: 26-27.

McMurtry, J. A. and Croft B. A., 1997, Life-styles of phytoseiid mites and their role in biological control, Annual Review of Entomology, Vol. 42: 291-321.

Nomikou, M., Janssen, A., Schraag, R. and Sabelis, M. W., 2001, Phytoseiid predators as biological control agents for *Bemisia tabaci*. Exp. Appl. Acarol. 25: 270-290

Parkinson, C. L., 1992, "Culturing free-living astigmatid mites." Arachnida: Proceedings of a one day symposium on spiders and their allies held on Saturday 21 Nov. 1987 at the Zoological Society of London, eds. Cooper, J. E., Pearce-Kelly, P, Williams, D. L., p. 62-70.

Ramakers, P. M. J. and Van Lieburg, M. J., 1982, Start of commercial production and introduction of *Amblyseius mckenzei* Sch. & Pr. (Acarina: Phytoseiidae) for the control of *Thrips tabaci* Lind. (Thysanoptera: Thripidae) in glasshouses, Med. Fac. Landbouww. Rijksuniv. Gent, 47/2, pp 541-545.

Ramakers, P. M. J., 1989, Large scale introductions of Phytoseiid predators to control *thrips* on cucumber, Med. Fac. Landbouww. Rijksuniv. Gent, 54/3a, pp 923-929.

Ramakers, P. M. J. and Voet, S. J. P., 1996, Introduction of *Amblyseius degenerans* for *thrips* control in sweet peppers with potted castor beans as banker plants. IOBC/WPRS working group on integrated control in glasshouses 19 (1): 127-130.

Rasmy et al., 1987, A new diet for reproduction of two predaceous mites *Amblyseius gossipi* and *Agistemus exsertus* (Acari: Phytoseiidae, Stigmaeidae), Entomophaga 32 (3), pp 277-280.

Romeih, A. H. M., El-Saidy, E. M. A. and El Arnaouty, S. A., 2004, Suitability Of Two Lepidopteran Eggs As Alternative Preys For Rearing Some Predatory Mites. The first Arab Conference of Applied Biological Pest Control, Cairo, Egypt, 5-7 Apr. 2004.

Swirski, E., Amitai, S. and Dorzia, N., 1967, Laboratory studies on the feeding, development and oviposition of the predaceous mite *Amblyseius rubini* Swirskii and Amitai an *Amblyseius swirskii* Athias-Henriot (Acarina: Phytoseiidae) on various kinds of food substances. Israel J. Agric. Res. 17:101-119

Sampson. C., 1998, The commercial development of an *Amblyseius cucumeris* controlled release method for the control of *Frankliniella occidentalis* in protected crops, The 1998 Brighton conference—Pests & Diseases, 5B-4, pp 409-416.

Solomon, M. E. and Cunnington, A. M., 1963, Rearing acaroid mites, Agricultural Research Council, Pest Infestation Laboratory, Slough, England, pp 399-403.

Teich, Y. 1966, Mites of the family of Phytoseiidae as predators of the tobacco whitefly, *Bemisia Ephestia tabaci* Gennadius. Israel J. Agric. Res. 16: 141-142.

Wei-Lan Ma and J. E. Laing, 1973, Biology—of *Amblyseius (Neoseiulus) californicus*, Entomophaga, 47-60.

The invention claimed is:

1. A mite composition comprising:
    a rearing population of a phytoseiid predatory mite species,
    a factitious host population comprising at least one species selected from the family of the *Carpoglyphidae*, and
    optionally a carrier for individuals of said populations.

2. The composition according to claim 1, wherein the phytoseiid predatory mite species comprises at least one species from the subfamily of *Amblyseiinae* or *Typhlodrominae*.

3. The composition according to claim 1, comprising a food substance suitable for said factitious host population.

4. The composition according to claim 1, wherein the factitious host population is a rearing population.

5. The composition according to claim 1, wherein the number of individuals of the phytoseiid predatory mite species relative to the number of individuals of the factitious host is from about 100:1 to 1:20.

6. A method for rearing a phytoseiid predatory mite comprising:
    providing a composition according to claim 1, and
    allowing individuals of said phytoseiid predatory mite to prey on individuals of said factitious host population.

7. A method according to claim 6, wherein the composition is maintained at least one condition selected from the group consisting of:
    18-35° C.; and
    60-95% relative humidity.

8. A method according to claim 6, wherein said composition comprises a carrier and a suitable food substance and the factitious host population is maintained as a three-dimensional culture on the carrier.

9. The method according to claim 6, wherein the phytoseiid mite comprises at least one species from the subfamily of *Amblyseiinae* or *Typhlodrominae*.

10. Rearing system for rearing a phytoseiid predatory mite, which system comprises a container holding the composition according to claim 1.

11. Rearing system according to claim 10, wherein said container comprises an exit for at least one mobile life stage of the phytoseiid mite.

12. Rearing system according to claim 11, wherein said exit is suitable for providing a sustained release of said at least one mobile life stage.

13. A method for controlling a pest in a crop, the method comprising:
    providing a composition according to claim 1 to said crop.

14. The method according to claim 13 wherein the pest is selected from white flies, thrips, spider mites or tarsonemid mites.

15. The method according to claim 13, wherein the providing comprises applying an amount of said composition in the vicinity of said crop.

16. The method according to claim 15, wherein the amount is from 1-10 ml.

17. The method according to claim 13, wherein the crop is selected from: (greenhouse) vegetable crops; soft fruit; (greenhouse) ornamental crops; or tree crops.

18. The composition according to claim 1, wherein the factitious host population comprises at least one species from the genus *Carpoglyphus*.

19. The composition according to claim 1, wherein the factitious host population comprises the species *Carpoglyphus lactis*.

20. The composition according to claim 1, wherein the phytoseiid predatory mite species comprises at least one species from the genus *Amblyseius, Euseius, Neoseiulus, Typhlodromalus, Typhlodromips, Galendromus,* or *Typhlodromus*.

21. The composition according to claim 1, wherein the phytoseiid predatory mite species comprises at least one of *Amblyseius andersoni, Amblyseius swirskii, Amblyseius largoensis, Euseius finlandicus, Euseius hibisci, Euseius ovalis, Euseius victoriensis, Euseius stipulatus, Euseius scutalis, Euseius tularensis, Euseius addoensis, Euseius citri, Neoseiulus barkeri, Neoseiulus califomicus, Neoseiulus cucumeris, Neoseiulus longispinosus, Neoseiulus womersleyi, Neoseiulus idaeus, Neoseiulus fallacis, Typhlodromalus limonicus, Typhlodromalus peregrinus, Typhlodromips montdorensis, Galendromus occidentalis, Typhlodromus pyri, Typhlodromus doreenae,* or *Typhlodromus athiasae*.

22. The composition according to claim 1, wherein the number of individuals of the phytoseiid predatory mite species relative to the number of individuals of the factitious host is from 1:1 to 1:10.

23. The composition according to claim 1, wherein the number of individuals of the phytoseiid predatory mite species relative to the number of individuals of the factitious host is 1:4.

24. The composition according to claim 1, wherein the number of individuals of the phytoseiid predatory mite species relative to the number of individuals of the factitious host is 1:5.

25. The composition according to claim 1, wherein the number of individuals of the phytoseiid predatory mite species relative to the number of individuals of the factitious host is 1:7.

26. The method according to claim 9, wherein the phytoseiid predatory mite species comprises at least one species from the genus *Amblyseius, Euseius, Neoseiulus, Typhlodromalus, Typhlodromips, Galendromus,* or *Typhlodromus*.

27. The method according to claim 9, wherein the phytoseiid predatory mite species comprises at least one of *Amblyseius andersoni, Amblyseius swirskii, Amblyseius largoensis, Euseius finlandicus, Euseius hibisci, Euseius ovalis, Euseius victoriensis, Euseius stipulatus, Euseius scutalis, Euseius tularensis, Euseius addoensis, Euseius citri , Neoseiulus barkeri, Neoseiulus californicus, Neoseiulus cucumeris, Neoseiulus longispinosus, Neoseiulus womersleyi, Neoseiulus idaeus, Neoseiulus fallacis, Typhlodromalus limonicus, Typhlodromalus peregrinus, Typhlodromips montdorensis, Galendromus occidentalis, Typhlodromus pyri, Typhlodromus doreenae,* or *Typhlodromus athiasae*.

28. The method according to claim 13, wherein the pest is *Trialeurodes vaporariorum, Bemisia tabaci, Thrips tabaci, Frankliniella occidentalis, Tetranychus urticae,* or *Polyphagotarsonemus latus.*

29. The method according to claim 15, wherein the amount is from 2-5 ml.

30. The method according to claim 13, wherein the crop is peppers (Capsicum annuum), eggplants (*Solanum melogena*), Curcubits (*Cucurbitaceae*), cucumbers (*Cucumis sativa*), melons (*Cucumis melo*), watermelons (*Citrullus lanatus*), strawberries (*Fragaria x ananassa*), raspberries (*Rubus ideaus*), roses, gerberas, chrysanthemums, or Citrus spp.

* * * * *

UNITED STATES PATENT AND TRADEMARK OFFICE
CERTIFICATE OF CORRECTION

| | | |
|---|---|---|
| PATENT NO. | : 7,947,269 B2 | Page 1 of 1 |
| APPLICATION NO. | : 11/793579 | |
| DATED | : May 24, 2011 | |
| INVENTOR(S) | : Karel Jozef Florent Bolckmans | |

It is certified that error appears in the above-identified patent and that said Letters Patent is hereby corrected as shown below:

In Claim 7 (Originally Claim 7), Section 15, line 44, after the word "at", insert the word at.

In Claim 21 (Originally Claim 26), Section 16, line 29, replace the word "califomicus" with the word californicus.

Signed and Sealed this
First Day of November, 2011

David J. Kappos
*Director of the United States Patent and Trademark Office*